United States Patent [19]

Hwang et al.

[11] Patent Number: 4,603,702
[45] Date of Patent: Aug. 5, 1986

[54] CIRCUIT FOR MONITORING CONTACT OF ULTRASOUND TRANSDUCER WITH PATIENT

[75] Inventors: Juin-Jet Hwang, Mesa; Ronald E. McKeighan, Tempe; Paul M. Jaeger, Mesa, all of Ariz.

[73] Assignee: Advanced Technology Laboratories, Inc., Bothell, Wash.

[21] Appl. No.: 710,358

[22] Filed: Mar. 11, 1985

[51] Int. Cl.[4] .............................................. A61B 10/00
[52] U.S. Cl. ................................................. 128/660
[58] Field of Search ............................. 128/660–661; 73/631, 609–615

[56] References Cited

U.S. PATENT DOCUMENTS

| | | | |
|---|---|---|---|
| 4,043,181 | 8/1977 | Nigam | 128/660 X |
| 4,154,114 | 5/1979 | Katy et al. | 128/660 X |
| 4,206,653 | 6/1930 | Le May | 128/660 X |
| 4,323,077 | 4/1982 | Smith | 128/660 |
| 4,501,151 | 2/1985 | Christman | 128/660 X |
| 4,537,199 | 8/1985 | Muravaka | 128/660 |

OTHER PUBLICATIONS

Wells, P. N. T. "Biomedical Ultrasonics", Academic Press, N.Y., 1977, pp. 443–448.

Primary Examiner—Kyle L. Howell
Assistant Examiner—Francis J. Jaworski
Attorney, Agent, or Firm—Lawrence S. Levinson; Sanford J. Asman

[57] ABSTRACT

A circuit for controlling a patient exposure timer used to measure the time which a patient has been exposed to ultrasound energy is disclosed. The circuit operates by measuring a signal representative of whether an ultrasound transducer is coupled to air or to a patient. If the transducer is coupled to a patient, then the exposure timer is turned on. In the case of a mechanical scanhead, such as an oscillating scanhead or a rotating scanhead, the exposure timer control circuit can also be used to control the mechanical movement of the scanhead itself.

1 Claim, 7 Drawing Figures

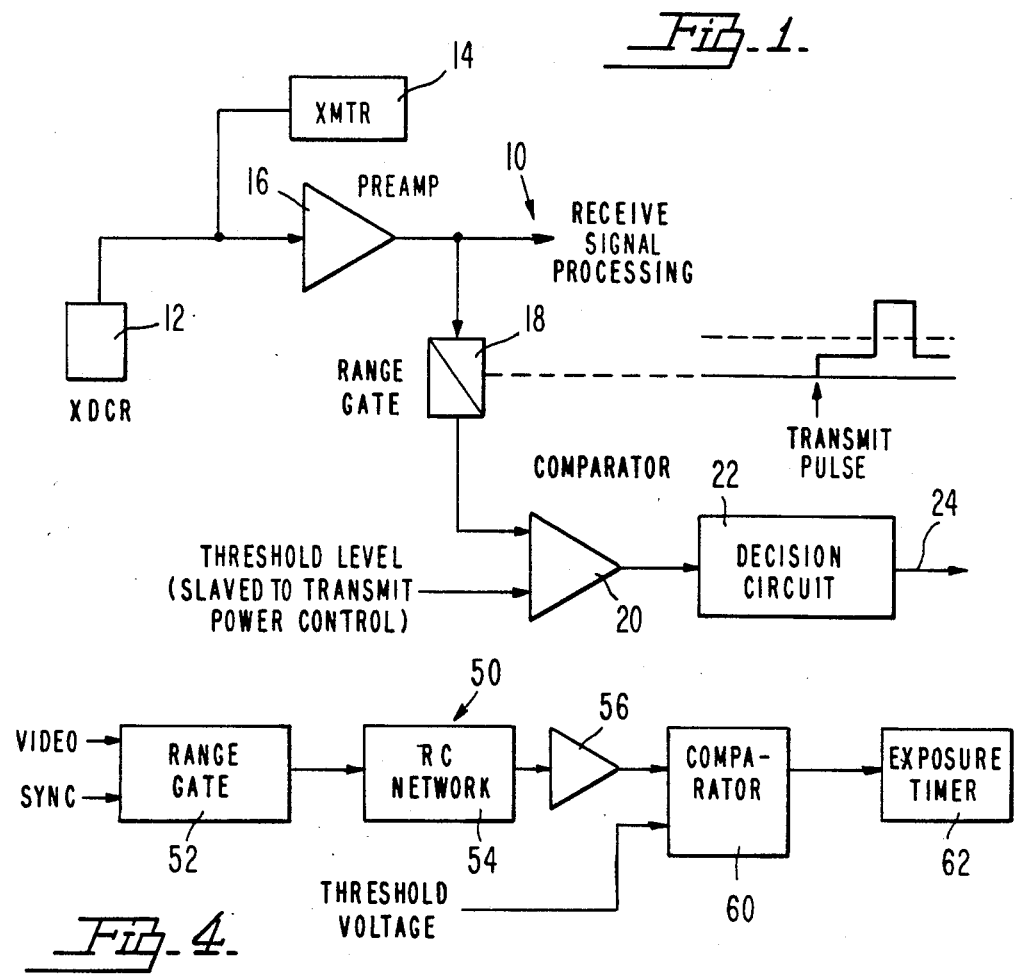
Fig. 1.
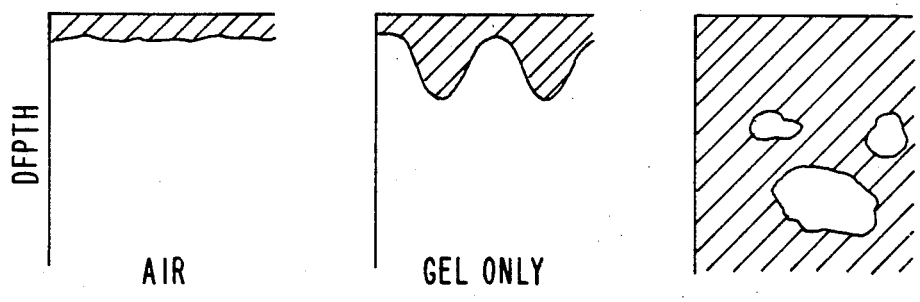
Fig. 4.
Fig. 3A.  Fig. 3B.  Fig. 3C.

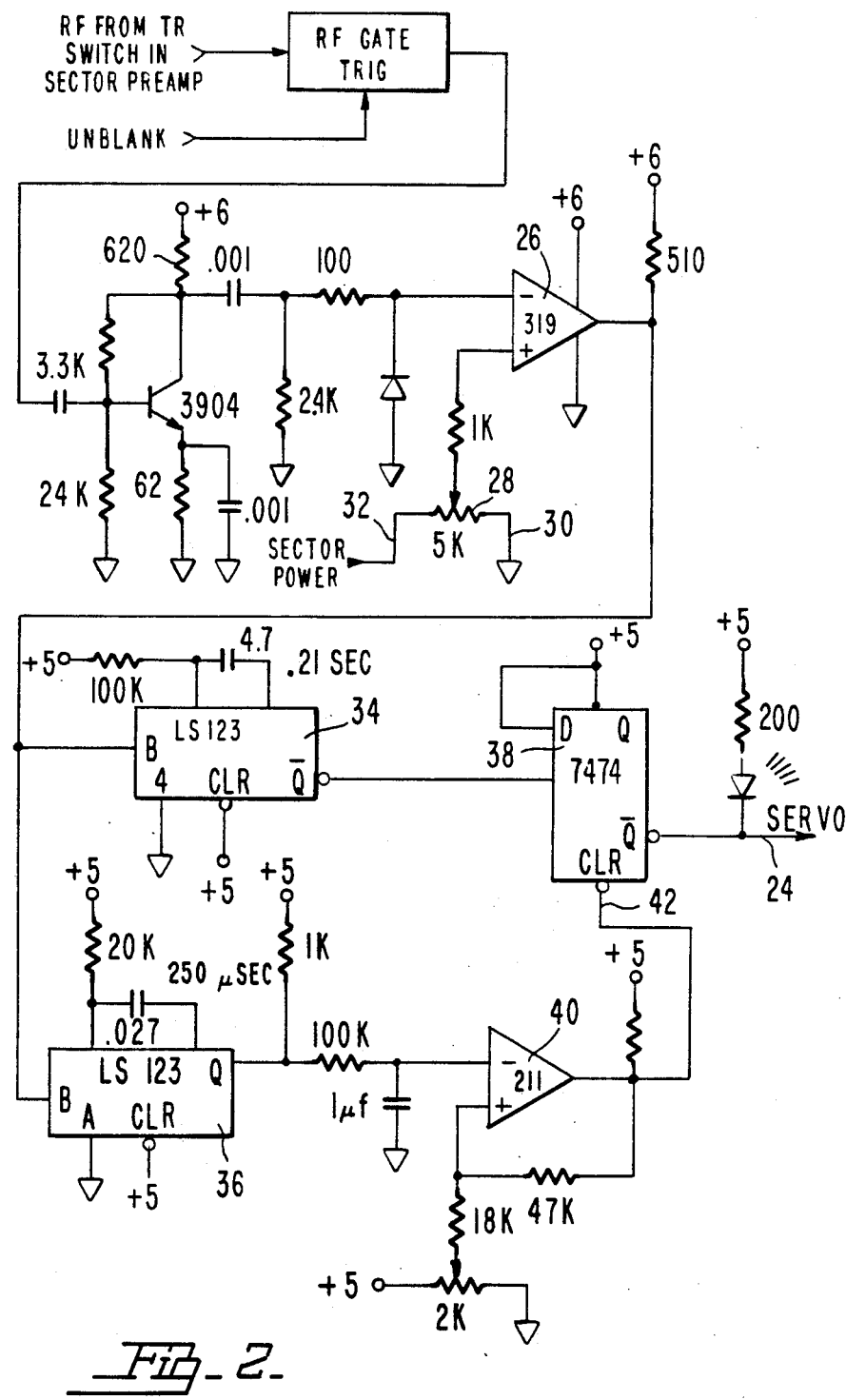
FIG_2

CIRCUIT FOR MONITORING CONTACT OF ULTRASOUND TRANSDUCER WITH PATIENT

BACKGROUND OF THE INVENTION

The present invention relates to a circuit for use in an ultrasound medical scanner. In particular, it relates to a circuit for use in an ultrasound medical scanner which is capable of measuring a patient's exposure to ultrasound energy.

Medical ultrasound scanners have been used for a number of years. They have always been considered to be safe, nonintrusive diagnostic devices. However, through the years various questions have been raised regarding the safety associated with exposing patients to ultrasound energy. In particular, there have been questions regarding whether it is safe to expose a developing fetus to ultrasound when a pregnant woman underoges a sonography. Accordingly, there has recently been published a series of guidelines associated with when it would be medically advisable to perform ultrasound scans of pregnant women. In addition, it has been suggested that it would be appropriate to measure the exposure of particular patients to ultrasound in order that appropriate research into the safety of ultrasound can be conducted. For these reasons, a device for measuring patient exposure to ultrasound energy would be desirable.

SUMMARY OF THE INVENTION

The present invention is a device which monitors a signal representative of contact between an ultrasound scanhead and a patient and provides an output signal which can be used to operate a timer which measures the amount of time a patient has been exposed to ultrasound.

In a first embodiment of the invention, the reverberation echo from the endcap of a mechanical ultrasound scanhead is measured. Such reverberation echoes drop dramatically when the scanhead endcap is in contact with a patient. Accordingly, a range gated signal (set to a range corresponding to the distance from the transducer to the endcap) is measured to determine if it is less than a particular threshold value, i.e., to see if there is patient contact. When the echo at the range associated with the transducer endcap is below a predetermined threshold value, a signal indicating patient contact is generated. That signal may be used to turn on a patient exposure timer. In the case of a mechanical sector scanner, i.e. either a "wobbler" or a rotating scanhead, the motor which provides mechanical movement to the scanhead may also be controlled by the output signal which indicates patient contact. Thus, the motor can be turned on when the reverberation signal is less than the preselected threshold value.

In a second embodiment of the invention, useable with linear transducers, the video signal beyond some threshold depth is measured and integrated. If the integrated video signal beyond the threshold depth is large enough, there is an indication that a patient is being monitored, so a signal representative of patient contact is generated. That signal may be used to turn on the ultrasound exposure timer.

BRIEF DESCRIPTION OF THE DRAWING

In the Drawing:

FIG. 1 is a block diagram of a first embodiment of the present invention;

FIG. 2 is a schematic diagram illustrating the components which comprise the block diagram of FIG. 1;

FIG. 3A is a representation of a screen display of a linear ultrasound unit in which a transducer is coupled only to air;

FIG. 3B is a representation of a screen display of a linear ultrasound unit in which there is ultrasound coupling gel on the linear scanhead.

FIG. 3C is a representation of a screen display of a linear ultrasound unit in which the transducer is coupled to a patient;

FIG. 4 is a block diagram of a second embodiment of the present invention in which a linear scanhead is used.

DETAILED DESCRIPTION OF THE PREFERRED EMBODIMENTS

Figure 5:
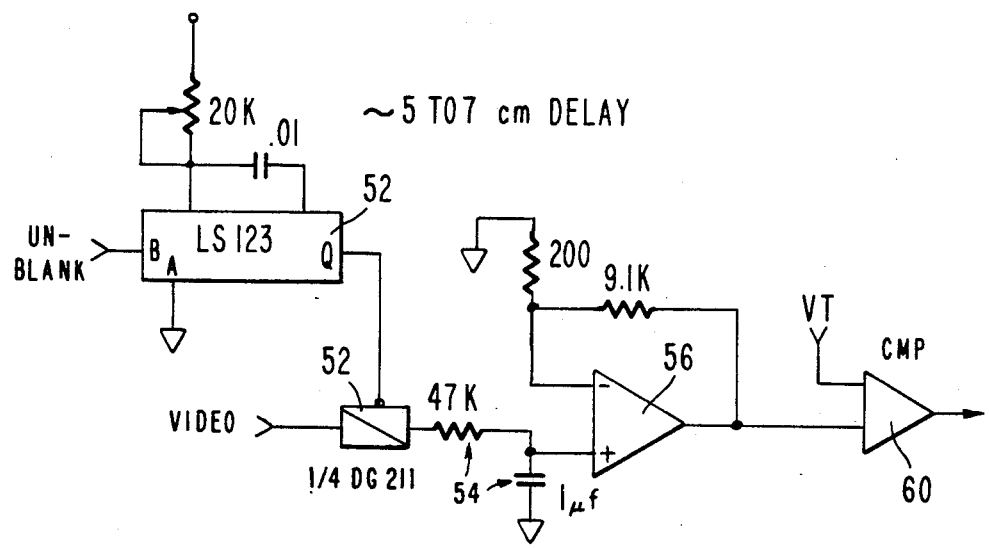
FIG. 5 is a schematic diagram showing the components which comprise the block diagram of FIG. 4.

Referring generally to FIG. 1, a block diagram of the first embodiment of the present invention is shown. The device 10 includes an ultrasound transducer 12 which is connected to an ultrasound transmitter 14 and a preamp 16. Connected also to the preamp 16 are range gated signal conditioning circuits 18 which lead to a comparator 20 and a decision circuit 22. A threshold level circuit (not shown), which is slaved to the transmitter power control, is also connected to the comparator 20. It has been found that when the range gate circuitry 18 is set to a range corresponding to the distance from the transducer 12 to the endcap of the scanhead, reverberation echoes which exceed the threshold level into the comparator 20 will be present when the scanhead endcap is not in contact with a patient. On the other hand, when the scanhead endcap is in intimate patient contact, there will be no high level reverberation echoes present, and the decision circuit 22 will generate an output signal on line 24 indicative of patient contact. An exposure timer circuit may be connected to the output line 24 of the decision circuit 22. The exposure timer and, optionally the motor drive for the transducer 12 (also connected to line 24) may be turned on when the output signal on line 24 indicates there is patient contact.

Referring now to FIG. 2, the specific circuitry utilized in the block diagram of FIG. 1 is shown. In the circuitry of FIG. 2 the threshold level comparator 20 is comprised of an operational amplifier 26 to which a threshold level is set by means of an adjustable potentiometer 28. One end 30 of the potentiometer 28 is connected to ground and the other end 32 is connected to the sector power, i.e. the transmit level control, voltage. The output of the operational amplifier 26 is used to drive a pair of flip flop circuits 34, 36. The first flip flop circuit 34 is connected to a third flip flop circuit 38 and the output of the second flip flop circuit 36 is connected by means of an operational amplifier 40 (connected as a comparator) to the clear pin 42 of the third flip flop circuit 38. Accordingly, if the first flip flop circuit 34 misses threshold outputs for some predetermined period of time, for example, approximately 0.2 seconds in the particular embodiment shown, the output signal on line 24 will be low indicating patient contact. The low output signal on line 24 may be used to turn on a patient exposure timer and, optionally, to turn on a servomechanism which drives the scanhead. If, however, the second flip flop circuit 36 receives threshold outputs, the third flip flop circuit 38 is cleared and the exposure timer and the servomechanism driving the scanhead are turned off by the high output signal on line 24.

Referring to FIGS. 3-5, a system for timing patient exposure which may be used with a linear transducer is illustrated. In FIG. 3A a representation of a screen display generated by a linear scanhead which is pointing into air is shown. As indicated, there will be some apparent echo at the interface between the scanhead and the air. In FIG. 3B, a representation of a screen display from a linear scanhead which has ultrasound coupling gel on it, but which is not coupled to a patient is shown; while in FIG. 3C a representation of a screen display of a linear scanhead which is coupled to a patient is shown. In each of the video displays shown in FIGS. 3A-3C, there is some signal level at depths which are close to the scanhead surface. However, below a predetermined threshold depth the amount of video signal which is present falls off rapidly for scanheads which are not coupled to patients. Accordingly, the video signal beyond some predetermined threshold depth may be integrated to obtain a value indicative of patient coupling.

Referring to FIG. 4, a circuit 50 which provides a running average of the video level beyond about five centimeters is shown. Five centimeters has been selected as an appropriate threshold depth, because reverberations from ultrasound coupling gel have been found to usually be between about zero and five centimeters from the scanhead surface. While five centimeters has been selected as an appropriate threshold depth, those skilled in the art will recognize that this setting maybe inadequate if a thick coating of coupling gel is placed on a scanhead surface.

The circuit (shown in FIGS. 4 and 5) is comprised of a range gate circuit 52 which feeds an RC averaging circuit 54. The output of the range gate circuit 52, which corresponds to the video signal beyond about five centimeters, is integrated using a resistor-capacitor network 54 which feeds into an operational amplifier 56. The output of the operational amplifier 56 is one of the inputs into a comparator 60 whose other input is a decision threshold voltage, $V_t$. As will be recognized by those skilled in the art, the decision threshold voltage, $V_t$, needs to be calculated from near gain, far gain, balance, power level, receiver gain control characteristics, transfer characteristics of the system, as well as anticipated signal strengths from tissue. The output of the comparator 60 on line 62 may be used to control a patient exposure timer.

We claim:
1. A circuit for monitoring contact of an ultrasound transducer with a patient and for generating an output signal which can be used to operate a timer which measures the amount of time said patient has been exposed to ultrasound energy comprising:
    (a) a medical ultrasound scanner of the type comprising an ultrasound transmitter, an ultrasound receiver, and ultrasound scanhead, said ultrasound scanhead being a mechanical scanhead of the type in which at least one ultrasound transducer is mechanically moved within said scanhead and ultrasound energy is transmitted out of said scanhead through an endcap;
    (b) monitoring means associated with said ultrasound receiver for monitoring a signal representative of the coupling of said ultrasound scanhead with said patient and for generating an output signal which indicates that said ultrasound transmitter is transmitting ultrasound energy into a patient, said monitoring means being comprised of a circuit which measures the amplitude of any reverberation echo from the endcap of said scanhead by measuring the intensity of the signal which is received by said ultrasound receiver at a time corresponding to the time it takes for ultrasound energy to travel from said transducer to said endcap and back, and in which said monitoring means compares the intensity of said reverberation echo to a predetermined threshold value; and
    (c) means associated with said monitoring means for controlling the mechanical movement of said scanhead when said monitoring means detects a reverberation echo which exceeds said threshold value.

* * * * *